United States Patent
Ludwig et al.

(10) Patent No.: US 8,647,680 B2
(45) Date of Patent: Feb. 11, 2014

(54) METHODS AND COMPOSITIONS FOR TREATMENT OF LESIONED SITES OF BODY VESSELS

(75) Inventors: Florian Niklas Ludwig, Mountain View, CA (US); Stephen Pacetti, San Jose, CA (US); Paul Consigny, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 216 days.

(21) Appl. No.: 12/789,002

(22) Filed: May 27, 2010

(65) Prior Publication Data

US 2010/0233263 A1 Sep. 16, 2010

Related U.S. Application Data

(62) Division of application No. 11/404,233, filed on Apr. 14, 2006, now Pat. No. 7,744,928.

(51) Int. Cl.
| | | |
|---|---|---|
| *A61K 9/14* | (2006.01) | |
| *A61K 33/00* | (2006.01) | |
| *A61K 31/198* | (2006.01) | |
| *A61P 9/10* | (2006.01) | |
| *A61M 25/00* | (2006.01) | |

(52) U.S. Cl.
USPC .................... 424/718; 424/484; 424/489

(58) Field of Classification Search
None
See application file for complete search history.

(56) References Cited

U.S. PATENT DOCUMENTS

| | | | |
|---|---|---|---|
| 5,498,421 A * | 3/1996 | Grinstaff et al. | 424/450 |
| 5,648,101 A | 7/1997 | Tawashi | |
| 5,676,963 A | 10/1997 | Keefer et al. | |
| 5,814,666 A * | 9/1998 | Green et al. | 514/611 |
| 5,861,168 A | 1/1999 | Cooke et al. | |
| 5,935,135 A | 8/1999 | Bramfitt et al. | |
| 6,153,186 A | 11/2000 | Stamler et al. | |
| 6,156,053 A | 12/2000 | Gandhi et al. | |
| 6,356,536 B1 | 3/2002 | Repke | |
| 6,425,881 B1 | 7/2002 | Kaesemeyer | |
| 6,569,688 B2 | 5/2003 | Sivan et al. | |
| 6,656,506 B1 | 12/2003 | Wu et al. | |

(Continued)

FOREIGN PATENT DOCUMENTS

| | | |
|---|---|---|
| EP | 1393723 | 3/2004 |
| WO | WO-0062614 | 10/2000 |

(Continued)

OTHER PUBLICATIONS

Bhorade et al. (Am J Respir Crit Care Med 1999, 159: pp. 571-579).*

(Continued)

*Primary Examiner* — Ernst Arnold
(74) *Attorney, Agent, or Firm* — Blakely, Sokoloff, Taylor & Zafman LLP

(57) ABSTRACT

Methods and compositions for inducing apoptosis of cells, such as macrophages, at a lesioned site of a body vessel are disclosed herein. Nitric oxide can be directly or indirectly delivered to a treatment site to increase macrophage apoptosis. Delivery can include site specific delivery of nitric oxide gas, nitric oxide in aqueous solution or a substance(s) which releases nitric oxide or causes nitric oxide to be generated from an endogenous source. Delivery can be achieved by a delivery system such as a catheter assembly, stent or other suitable device.

8 Claims, 3 Drawing Sheets

(56) References Cited

U.S. PATENT DOCUMENTS

| | | | |
|---|---|---|---|
| 6,780,849 B2* | 8/2004 | Herrmann et al. | 514/23 |
| 7,022,334 B1 | 4/2006 | Ding | |
| 2002/0082221 A1 | 6/2002 | Herrmann et al. | |
| 2002/0094985 A1 | 7/2002 | Herrmann et al. | |
| 2004/0197274 A1* | 10/2004 | Fein et al. | 424/45 |
| 2005/0145258 A1 | 7/2005 | Dong | |
| 2005/0249777 A1 | 11/2005 | Michal et al. | |

FOREIGN PATENT DOCUMENTS

| | | |
|---|---|---|
| WO | WO-03017989 | 3/2003 |
| WO | WO-2005070008 | 8/2005 |
| WO | WO-2007097875 | 8/2007 |

OTHER PUBLICATIONS

Abbott Cardiovascular Systems, PCT Search Report and Written Opinion dated Oct. 30, 2007 for PCT/US2007/008934.

Abbott Cardiovascular Systems, Final office action dated Aug. 3, 2009 for U.S. Appl. No. 11/404,233.

Baggio, R., et al., "Biochemical and functional profile of a newly developed potent and isozyme-selective arginase inhibitor", Journal of Pharmacology and Experimental Therapeutics, vol. 290, No. 3, (1999), 1409-1416.

Berkowitz, D. E., et al., "Arginase reciprocally regulates nitric oxide synthase activity and contributes to endothelial dysfunction in aging blood vessels", Circulation, vol. 108, (2003), 2000-2006.

Boyle, J. J., et al., "Human macrophage-induced vascular smooth muscle cell apoptosis requires NO enhancement of Fas/Fas-L interactions", Arteriosclerosis, Thrombosis and Vascular Biology, vol. 22, (2002), 1624-1630.

Gotoh, T., et al., "Arginase II down regulates nitric oxide (NO) production and prevents NO-mediated apoptosis in murine macrophage-derived RAW 264.7 cells", Journal of Cell Biology, vol. 144, No. 3, (Feb. 8, 1999), 427-434.

Li, H., et al., "Activities of arginase I and II are limiting for endothelial cell proliferation", Am J Physiol Regulatory Integrative Comp Physiol, vol. 282, (2002), R64-R69.

Niebauer, J., et al., "Local L-arginine delivery after balloon angioplasty reduces monocyte binding and induces apoptosis", Circulation, vol. 100, (1999), 1830-1835.

Pulker, S. K., et al., "Incorporation of nitric oxide-releasing crosslinked polyethyleneimine microspheres into vascular grafts", Journal of Biomedical Materials Research, vol. 37, No. 2, (Nov. 1997), 182-189.

Schwarzacher, S P., et al., "Local intramural delivery of L-arginine enhances nitric oxide generation and inhibits lesion formation after balloon angioplasty", Circulation, (1997), 1863-1869.

Tuomisto, T. T., et al., "Gene expression in macrophage-rich inflammatory cell infiltrates in human atherosclerotic lesions as studied by laser microdissection and DNA array", Arteriosclerosis, Thrombosis and Vascular Biology, vol. 23, (2003), 2235-2240.

Wang, B. Y., et al., "Regression of atherosclerosis: role of nitric oxide and apoptosis", Circulation, vol. 99, (1999), 1236-1241.

Wei, L. H., et al., "Elevated arginase I expression in rat aortic smooth muscle cells increases cell proliferation", Proceedings of the National Academy of Sciences, vol. 98, (2001), 9260-9264.

* cited by examiner

METHODS AND COMPOSITIONS FOR TREATMENT OF LESIONED SITES OF BODY VESSELS

CROSS-REFERENCE TO RELATED APPLICATION

The application is a divisional of co-pending U.S. patent application Ser. No. 11/404,233, filed Apr. 14, 2006 now U.S. Pat. No. 7,744,928 and incorporated herein by reference.

FIELD OF INVENTION

Methods and compositions for treating lesioned sites of atherosclerotic physiological vessels using nitric oxide sources.

BACKGROUND OF INVENTION

"Arteriosclerosis" refers to the thickening and hardening of arteries. "Atherosclerosis" is a type of arteriosclerosis in which cells including smooth muscle cells and macrophages, fatty substances, cholesterol, cellular waste product, calcium and fibrin build up in the inner lining of a body vessel. If unstable or prone to rupture, the resultant build-up is commonly referred to as vulnerable plaque. It is generally believed that atherosclerosis begins with damage to the inner arterial wall resulting in a lesion. At the damaged site, substances such as lipids, platelets, cholesterol, cellular waste products and calcium deposit in the vascular tissue may accumulate, leading to plaque progression and potentially the formation of vulnerable plaque. In turn, these substances lead to recruitment of cells involved in the inflammatory cascade of the immune system, such as macrophages, which may release substances leading to plaque destabilization.

Artherosclerotic lesions are characterized by a high content of macrophages which contribute to atherosclerosis by, for example, releasing free radicals, synthesizing bioreactive lipids, synthesizing complement components, synthesizing coagulation cascade components, secreting proteases and protease inhibitors, secreting cytokines and chemokines and phagocytosis of apoptic cells.

"Apoptosis" is the disintegration of cells into membrane-bound particles that are then eliminated by phagocytosis or by shedding. Research studies suggest that nitric oxide induces macrophage cell apoptosis. For example, a recent study has shown that the oral administration of L-arginine, a substrate which releases nitric oxide, results in increased apoptosis of macrophage cells (Wang et al., 1999. Circulation 99; 1236-1241). Thus, macrophage apoptosis at lesioned sites of a body vessel is therefore desirable.

SUMMARY OF INVENTION

In accordance with embodiments of the present invention, nitric oxide can be directly or indirectly delivered to a treatment site or region of a body vessel to increase macrophage apoptosis. Delivery can include site specific delivery of nitric oxide gas, nitric oxide in aqueous solution or a substance(s) which releases nitric oxide or causes nitric oxide to be generated from an endogenous source, hereinafter collectively referred to as "nitric oxide sources." Delivery can be achieved by a delivery system such as a catheter assembly, stent or other suitable device.

DETAILED DESCRIPTION

Methods and compositions for inducing apoptosis of macrophage cells at a lesioned site of a body vessel, such as a blood vessel, using nitric oxide sources are disclosed herein. It is to be understood that reference to a lesioned site of a blood vessel is intended to include the treatment of one or more lesioned sites, as well as treatment of one or more regions, treatment sites, or injury sites of a blood vessel. Thus, the use of such terms may be referred to interchangeably herein and are intended to be included within the scope of the present invention.

Figure 1:
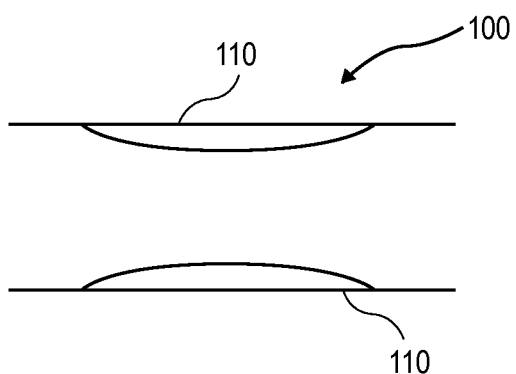
FIG. 1 illustrates a cross-sectional view of a diseased blood vessel.

FIG. 1 illustrates an occluded blood vessel 100 with plaque build-up 110. The injury site 110 can result in the increase of macrophage cells which accumulate modified low-density lipoprotein (LDL) and turn into foam cells. Macrophage and foam cells secrete growth factors, cytokines and other inflammatory mediators which influence the growth and development of other cell types within the atherosclerotic lesion, and the recruitment of monocytes to the lesion. Macrophage-derived foam cells release lipids into the intima (inner layer) of the blood vessel resulting in increased plaque build-up 110. In addition, macrophage released growth factors cause proliferation of smooth muscle cells and the plaque becomes fibrotic.

Methods for Inducing Macrophage Apoptosis

An excess amount of nitric oxide in macrophage cells can result in increased macrophage apoptosis. Under normal conditions, macrophage cells produce nitric oxide to regulate various biological functions. An overproduction of nitric oxide, however, may be toxic to macrophage cells resulting in apoptosis. In accordance with the present invention, nitric oxide can be directly or indirectly delivered to a treatment site 110 to increase macrophage apoptosis. Delivery can include site specific delivery of nitric oxide gas, nitric oxide in aqueous solution or a substance(s) which releases nitric oxide or causes nitric oxide to be generated from an endogenous source, or substances that increase the amount of nitric oxide produced endogenously. Delivery can be achieved by a delivery system such as a catheter assembly, stent or other suitable device.

Compositions

In some embodiments, nitric oxide gas can be directly delivered to a lesioned site for treatment thereof. In some embodiments, nitric oxide gas can be diluted with a physiologically acceptable carrier gas for delivery to a lesioned site thereof. Representative examples of physiologically acceptable carrier gases include, but are not limited to, carbon dioxide, nitrogen, argon, helium, and perfluoro gases such as perfluoropentane or perfluoropropane. For example, small amounts of nitric oxide may be mixed into perfluoropropane before introduction into a vessel.

In some embodiments, nitric oxide gas can be mixed with a solvent (other than aqueous solutions such as saline or physiological buffers) which is physiologically suitable for injection for delivery to a lesioned site thereof. Such solvents include, but are not limited to, ethanol, dimethylsulfoxide, n-methylpyrrolidone, benzyl alcohol, benzylbenzoate and ethyl acetate. The solvent phase containing nitric oxide gas may be mixed with or emulsified into an aqueous solution such as saline. Alternatively, the nitric oxide may be mixed with one or more of a contrast agent, including, but not limited to, Omnipaque®, Imagopaque®, Optiray®, or Iopamido®.

In some embodiments, nitric oxide gas can be mixed with aqueous solutions to create an aqueous solution for delivery to a lesioned site thereof. The solution may be partially saturated, saturated or super-saturated. A "saturated solution" is one in which a solvent has dissolved all of a solute possible at a given temperature. A "super-saturated solution" is one in which a solvent holds more solute than it normally holds at a given temperature as it is cooling down. A super-saturated solution may be stabilized by addition of surfactants such as PVA (poly vinyl alcohol), PVP (poly vinyl pyrrolidone), lipids, including phospholipids, amphiphilic polymers such as polyethylene glycol-polylactide (PEG-PLA) and ionic surfactants such as sodium dodecyl sulfate (SDS). Although nitric oxide has limited solubility in water (2-3 mM), it is believed that even a small or smaller quantity (e.g., less than about 2-3 mM) in solution delivered to a lesioned site can have beneficial effects.

In any of the above-described embodiments, the nitric oxide gas or nitric oxide gas solution may be encapsulated or formulated within a carrier for sustained release thereof. Carriers can include, but are not limited to, an implantable medical device, microspheres, nanoparticles, a gel or gel depot, a hydrogel or hydrogel depot, or a polymer or polymer depot for delivery and sustained release thereof. Carriers and methods of formulating substance-loaded carriers are known by those skilled in the art, an example of which can be found in U.S. Pat. No. 6,656,506 to Wu et al., incorporated by reference herein.

In some embodiments, L-arginine or polypeptides of L-arginine can be encapsulated or formulated within a carrier such as, for example, an implantable medical device, microspheres, nanoparticles, a gel or gel depot, a hydrogel or hydrogel depot, or a polymer or polymer depot for delivery and sustained release thereof. In the body of a mammal, nitric oxide is formed by the action of an endogenous enzyme, nitric oxide synthase (NOS), on L-arginine resulting in the production of nitric oxide and citrulline. Nitric oxide synthases includes endothelial nitric oxide synthase (eNOS, NOS I), inducible nitric oxide synthase (iNOS, NOS II) and neuronal nitric oxide synthase (nNOS, NOS III). iNOS is expressed in macrophages in response to various cytokines and microbial products. Once delivered to the treatment site, the L-arginine or polypeptides of L-arginine can diffuse from the carrier and provide more substrate by which iNOS can act upon to produce a greater population of NO within the localized treatment site. Other compounds suitable for formulation and delivery include, but are not intended to be limited to, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosine, bradykinin, calreticulin, bisacodyl, and phenolphthalein. For example, L-arginine may be encapsulated in nanoparticles of from between about 250 nm to about 300 nm in diameter by water-oil-water emulsification. In the emulsification process, L-arginine is dissolved in an aqueous solution, which is added to a polymer-solvent phase, for example polylactic glycolic acid (PLGA) dissolved in acetone. The aqueous phase containing the peptide is emulsified into the polymer phase by application of energy, for example by sonification. This emulsion is then added to an aqueous solution containing a small amount of an emulsifying agent such as poly-vinyl alcohol, and a water-oil-water emulsion is formed by addition of energy, for example by sonication. L-arginine loaded polymer particles are formed by removal of the acetone and may be lyophilized for storage.

In some embodiments, L-arginine and NOS can be encapsulated in an activated-release carrier such as a microsphere, nanoparticle, and the like. In some embodiments, the activated-release carrier can be permeable to both water and nitric oxide gas. Upon delivery, water can serve as the activating mechanism to start the enzymatic reaction of NOS on L-arginine. Once the reaction starts, nitric oxide gas can diffuse out of the activated-release carrier.

In some embodiments, a nitric oxide donor (NO donor), i.e., a nitric oxide-containing compound, and a suitable reactant (or no reactant) can be encapsulated in an activated-release carrier such as, for example, a microsphere, nanoparticle and the like. There are generally three kinds of mechanisms in which NO donors release NO: (I) spontaneously through thermal or photochemical self-decomposition; (II) chemical reactions with acid, alkali, metal and thiol; and (III) metabolic activation by NO synthases or oxidases. These NO donors may be mono-nitrosylated, poly-nitrosylated, mono-nitrosated and/or poly-nitrosated or a combination thereof at a variety of naturally susceptible or artificially provided binding sites for biologically active forms of NO.

In category I, for example, the NO donor can be the family of NONOates (diazeniumdiolates), which include, but are not limited to, O(2)-(2,4-Dinitrophenyl) 1-[(4-ethoxycarbonyl) piperazin-1-yl]diazen-1-ium-1,2-diolate (JS-K), N-FU/NONOate, S-nitrosocaptopril and Man-1-SNAP. In one example, JS-K can be attacked by the nucleophilic thiol group of glutathione resulting in the formation of a Meisenheimer complex. The NONOate moiety (4-carbethoxy-PIPERAZI/NO) then dissociates from the complex. At physiological conditions, the NONOate decomposes to release nitric oxide. Other examples include furoxanes.

In category II, for example, the NO donor can be a nitrite or nitrate such as sodium nitrite. A suitable reactant can include an appropriate reducing agent, such as sodium iodide, dithiothreitol, mercaptoethanol, iron particles, zinc particles, magnesium particles, sodium sulfide, sodium dithionite or sodium metabisulfite. When combined, the reducing agent reduces the nitric oxide donor such that the nitric oxide moiety disassociates from the metal ion. In some embodiments, the activated-release carrier can be permeable to both water and nitric oxide. Upon delivery, water can serve as an activator to start the reaction.

Other examples for NO donors are compounds comprising at least one ON—O—, ON—N— or ON—C— group. The compounds that include at least one ON—O—, ON—N— or ON—C— group are preferably ON—O—, ON—N— or ON—C-polypeptides; ON—O, ON—N— or ON—C— amino acids (including natural and synthetic amino acids and their stereoisomers and racemic mixtures); ON—O—, ON—N— or ON—C-sugars; ON—O—, ON—N— or ON—C— modified or unmodified oligonucleotides (comprising at least about 5 nucleotides, preferably from about 5 nucleotides to about 200 nucleotides); ON—O—, ON—N— or ON—C— straight or branched, saturated or unsaturated, aliphatic or aromatic, substituted or unsubstituted hydrocarbons; and ON—O—, ON—N— or ON—C-heterocyclic compounds. The term "polypeptide" as used herein includes proteins and polyamino acids that do not possess an ascertained biological function, and derivatives and mimics thereof.

Another group of NO donors include nitrates that donate, transfer or release nitric oxide, such as compounds comprising at least one $O_2N$—O—, $O_2N$—N—, $O_2N$—S— or $O_2N$—C— group. Preferred among these compounds are $O_2N$—O—, $O_2N$—N—, $O_2N$—S— or $O_2N$—C— polypeptides; $O_2N$—O—, $O_2N$—N—, $O_2N$—S— or $O_2N$—C— amino acids (including natural and synthetic amino acids and their stereoisomers and racemic mixtures); $O_2$ N—O—, $O_2N$—N—, $O_2N$—S— or $O_2N$—C-sugars; $O_2N$—O—; $O_2N$—N—, $O_2N$—S— or $O_2N$—C— modified and unmodified oligonucleotides; $O_2N$—O—, $O_2N$—N—, $O_2N$—S— or $O_2N$—C— straight or branched, saturated or unsaturated, aliphatic or aromatic, substituted or unsubstituted hydrocarbons; and $O_2N$—O—, $O_2N$—N—, $O_2N$—S— or $O_2N$—C— heterocyclic compounds. Preferred examples of compounds comprising at least one $O_2N$—O—, $O_2N$—N—, $O_2N$—S— or $O_2N$—C— group include isosorbide dinitrate, isosorbide mononitrate, clonitrate, erythrityltetranitrate, mannitol hexanitrate, nitroglycerin, pentaerythritoltetranitrate, pentrinitrol and propatylnitrate.

In some embodiments, a nitric oxide generator (NO generator), i.e., nitric oxide-containing compound, and a suitable catalytic agent can be encapsulated in an activated-release carrier such as a microsphere or nanoparticle. Examples of NO generators include, but are not limited to, nitrosylated proteins with cysteine residues which allow for nitrosylation at the thiol group. Examples of catalytic agents include, but are not limited to, copper ion complexes which cleave NO moieties from nitrosylated proteins. Other examples for NO donor substrates are S-nitrosothiols, which are compounds that include at least one —S—NO group. These compounds include S-nitroso-polypeptides; S-nitrosylated amino acids (including natural and synthetic amino acids and their stereoisomers and racemic mixtures and derivatives thereof); S-nitrosylated sugars; S-nitrosylated, modified and unmodified, oligonucleotides; straight or branched, saturated or unsaturated, aliphatic or aromatic, substituted or unsubstituted S-nitrosylated hydrocarbons; and S-nitroso heterocyclic compounds. In some embodiments, the activated-release carrier can be permeable to both water and nitric oxide. Upon delivery, water can serve as an activator to start the reaction.

In some embodiments, a drug which inhibits the enzymes arginases I and II (arginase inhibitors) can be delivered to the lesioned site for treatment thereof. Arginases I and II control the production of nitric oxide from L-arginine by NOS I, II and III within macrophage cells. By inhibiting arginase I and II, more L-arginine will be available as a substrate to produce nitric oxide gas. Examples of arginase inhibitors include, but are not limited to, (S)-(2-Boronoethyl)-L-cysteine and $N^\omega$-Hydroxy-nor-L-arginine. In some embodiments, substrates such as antisense oligonucleotides or small interfering RNA (siRNA) can be introduced to macrophage cells at the lesioned site to reduce arginase expression.

The nitric oxide donors, generators, substrates or gas may be co-formulated with a variety of pharmaceutical excipients such as pharmaceutically acceptable organic or inorganic carrier substances suitable for parenteral application which do not deleteriously react with the active compounds. Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethical fatty acid esters, hydroxymethyl-cellulose, polyvinylpyrrolidone, and the like.

In addition, nitric oxide donors, generators or substrates may be formulated for sustained release into an implantable medical device, micro- or nanoparticles made from polymer or ceramic materials, a gel or hydrogel depot or a polymer depot.

Delivery Systems and Methods

A variety of delivery systems known in the art can be used to deliver nitric oxide gas, nitric oxide solutions, or a substance(s) which releases nitric oxide or causes nitric oxide to be generated from an endogenous source, i.e., nitric oxide sources, to a treatment site. The delivery systems include, but are not intended to be limited to, regional, local and direct delivery systems and injection systems, in addition to stent deployment systems, and the like.

Figure 2:
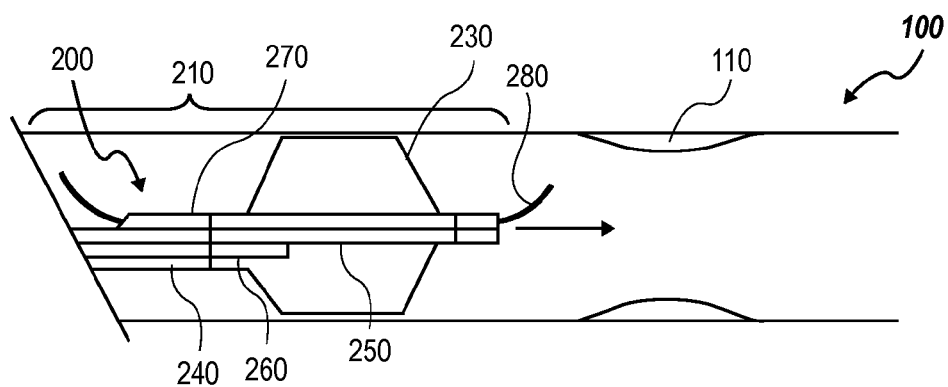
FIG. 2 illustrates a cross-sectional view of the blood vessel of FIG. 1 and a first embodiment of a catheter assembly to deliver a nitric oxide source to a blood vessel.
Figure 2:
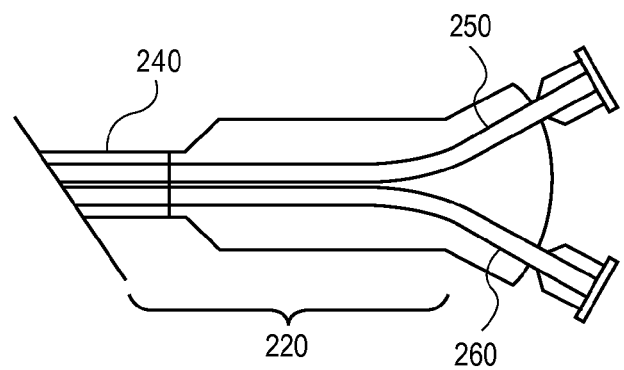

FIG. 2 shows blood vessel 100 having catheter assembly 200 disposed therein. Catheter assembly 200 includes proximal portion 220 and distal portion 210. Proximal portion 220 may be external to blood vessel 100 and to the patient. Representatively, catheter assembly 200 may be inserted through a femoral artery and through, for example, a guide catheter and with the aid of a guidewire to a location in the vasculature of a patient. That location may be, for example, a coronary artery. FIG. 2 shows distal portion 210 of catheter assembly 200 positioned proximal or upstream from treatment site 110.

In one embodiment, catheter assembly 200 includes primary cannula 240 having a length that extends from proximal portion 220 (e.g., located external through a patient during a procedure) to connect with a proximal end or skirt of balloon 230. Primary cannula 240 has a lumen therethrough that includes inflation cannula 260 and delivery cannula 250. Each of inflation cannula 260 and delivery cannula 250 extends from proximal portion 220 of catheter assembly 200 to distal portion 210. Inflation cannula 260 has a distal end that terminates within balloon 230. Delivery cannula 250 extends through balloon 230.

Catheter assembly 200 also includes guidewire cannula 270 extending, in this embodiment, through balloon 230 through a distal end of catheter assembly 200. Guidewire cannula 270 has a lumen sized to accommodate guidewire 280. Catheter assembly 200 may be an over the wire (OTW) configuration where guidewire cannula 270 extends from a proximal end (external to a patient during a procedure) to a distal end of catheter assembly 200. Guidewire cannula 230 may also be used for delivery of a substance such as a nitric oxide source when guidewire 280 is removed with catheter assembly 200 in place. In such case, separate delivery cannula (delivery cannula 250) is unnecessary or a delivery cannula may be used to deliver one substance while guidewire cannula 270 is used to delivery another substance.

In another embodiment, catheter assembly 200 is a rapid exchange (RX) type catheter assembly and only a portion of catheter assembly 200 (a distal portion including balloon 230) is advanced over guidewire 280. In an RX type of catheter assembly, typically, the guidewire cannula/lumen extends from the distal end of the catheter to a proximal guidewire port spaced distally from the proximal end of the catheter assembly. The proximal guidewire port is typically spaced a substantial distance from the proximal end of the catheter assembly. FIG. 2 shows an RX type catheter assembly.

In one embodiment, catheter assembly 200 is introduced into blood vessel 100 and balloon 230 is inflated (e.g., with a suitable liquid through inflation cannula 260) to occlude the blood vessel. Following occlusion, a nitric oxide source is introduced through delivery cannula 250. By introducing the nitric oxide source, the nitric oxide source can absorb on the walls of the blood vessel at treatment site 110.

Figure 3:
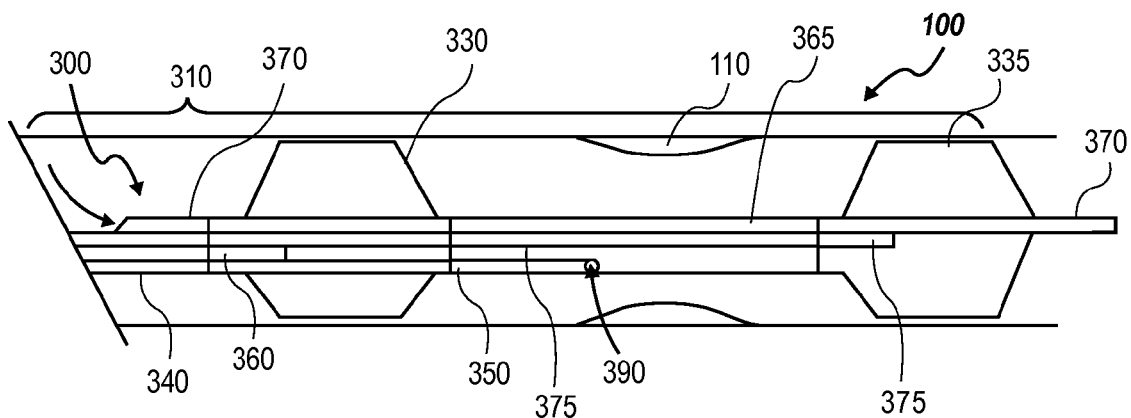
FIG. 3 illustrates a cross-sectional view of the blood vessel of FIG. 1 and a second embodiment of a catheter assembly to deliver a nitric oxide source to a blood vessel.
Figure 3:
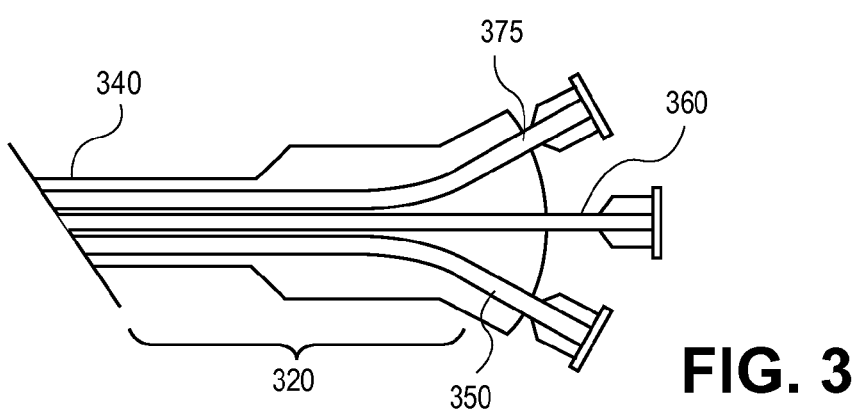

In an effort to improve the target area of nitric oxide sources to a treatment site, such as treatment site 110, the injury site may be isolated prior to delivery. FIG. 3 shows an embodiment of a catheter assembly having two balloons where one balloon is located proximal to treatment site 110 and a second balloon is located distal to treatment site 110. FIG. 3 shows catheter assembly 300 disposed within blood vessel 100. Catheter assembly 300 includes distal portion 310 and proximal portion 320 (external to a patient). Catheter assembly 300 has a tandem balloon configuration including proximal balloon 330 and distal balloon 335 aligned in series at a distal portion of the catheter assembly. Catheter assembly 300 also includes primary cannula 340 having a length that extends from a proximal end of catheter assembly 300 (e.g., located external to a patient during a procedure) to connect with a proximal end or skirt of balloon 330. Primary cannula 340 has a lumen therethrough that includes first inflation cannula 360 and second inflation cannula 375. First inflation cannula 360 extends from a proximal end of catheter assembly 300 to a point within balloon 330. First inflation cannula 360 and second inflation cannula 375 have lumens therethrough allowing balloon 330 and balloon 335 to be inflated, respectively. Thus, in this embodiment, balloon 330 is inflated through an inflation lumen separate from the inflation lumen that inflates balloon 335. First inflation cannula 360 has a lumen therethrough allowing fluid to be introduced in the balloon 330 to inflate the balloon. In this manner, balloon 330 and balloon 335 may be separately inflated. Each of first inflation cannula 360 and second inflation cannula 375 extends from, in one embodiment, the proximal portion 320 of catheter assembly 300 through a point within balloon 330 and balloon 335, respectively.

Catheter assembly 300 also includes guidewire cannula 370 extending, in this embodiment, through each of balloon 330 and balloon 335 through a distal end of catheter assembly. Guidewire cannula 370 has a lumen therethrough sized to accommodate a guidewire. No guidewire is shown within guidewire cannula 370. Catheter assembly 300 may be an over the wire (OTW) configuration or a rapid exchange (RX) type catheter assembly. FIG. 3 illustrates an RX type catheter assembly.

Catheter assembly 300 also includes delivery cannula 350. In this embodiment, delivery cannula 350 extends from a proximal portion 320 of catheter assembly 300 through a location between balloon 330 and balloon 335. Secondary cannula 365 extends between balloon 330 and balloon 335. A proximal portion or skirt of balloon 335 connects to a distal portion 310 of secondary cannula 365. A distal end or skirt of balloon 330 is connected to a proximal end of secondary cannula 365. Delivery cannula 350 terminates at opening 390 through secondary cannula 365. In this manner, a nitric oxide source may be introduced between balloon 330 and balloon 335 positioned adjacent to treatment site 110.

FIG. 3 shows balloon 330 and balloon 335 each inflated to occlude a lumen of blood vessel 100 and isolate treatment site 110. In one embodiment, each of balloon 330 and balloon 335 are inflated to a point sufficient to occlude blood vessel 100 prior to the introduction of a nitric oxide source. The nitric oxide source may then be introduced.

In the above embodiment, separate balloons having separate inflation lumens are described. It is appreciated, however, that a single inflation lumen may be used to inflate each of balloon 330 and balloon 335. Alternatively, in another embodiment, balloon 330 may be a guidewire balloon configuration such as a PERCUSURG™ catheter assembly where catheter assembly 300 including only balloon 330 is inserted over a guidewire including balloon 335.

Figure 4:
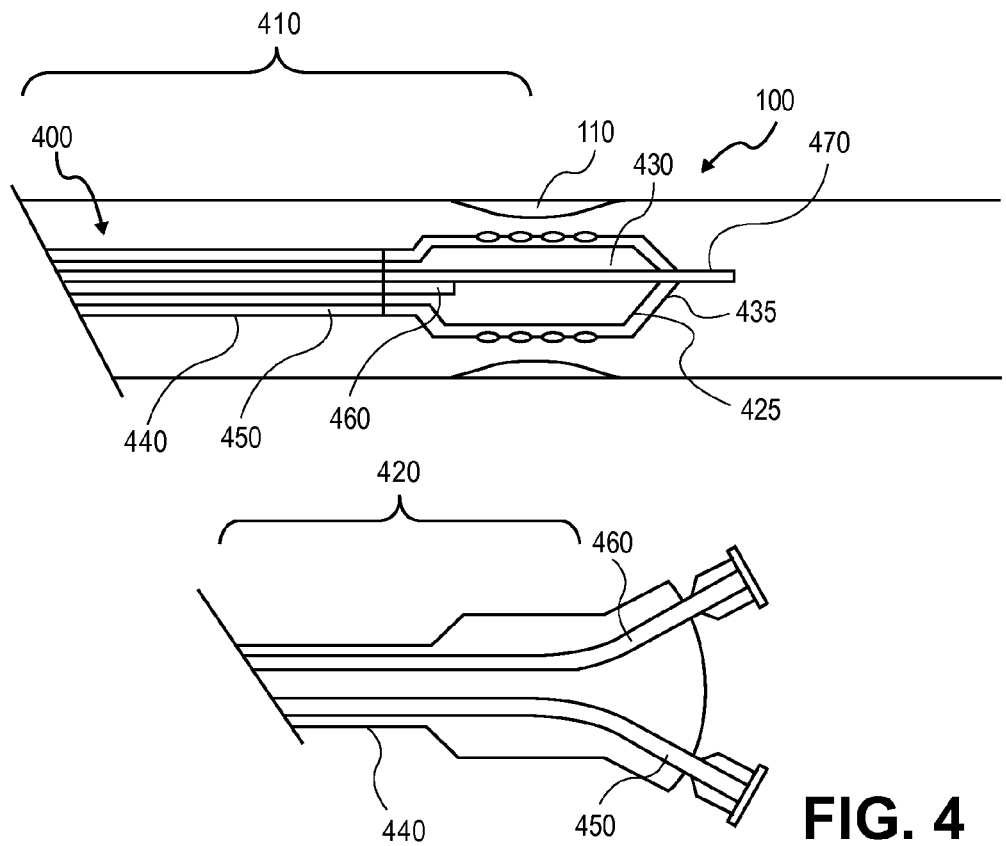
FIG. 4 illustrates a cross-sectional view of the blood vessel of FIG. 1 and a third embodiment of a catheter assembly to deliver a nitric oxide source to a blood vessel.

FIG. 4 shows another embodiment of a catheter assembly. Catheter assembly 400, in this embodiment, includes a porous balloon through which a substance, such as a nitric oxide source, may be introduced. FIG. 4 shows catheter assembly 400 disposed within blood vessel 100. Catheter assembly 400 has a porous balloon configuration positioned at treatment site 110. Catheter assembly 400 includes primary cannula 440 having a length that extends from a proximal portion 420 of catheter assembly 400 (e.g., located external to a patient during a procedure) to connect with a proximal end or skirt of balloon 430 at distal portion 410. Primary cannula 440 has a lumen therethrough that includes inflation cannula 460. Inflation cannula 460 extends from a proximal end of catheter assembly 400 to a point within balloon 430. Inflation cannula 460 has a lumen therethrough allowing balloon 430 to be inflated through inflation cannula 460.

Catheter assembly 400 also includes guidewire cannula 470 extending, in this embodiment, through balloon 430. Guidewire cannula 470 has a lumen therethrough sized to accommodate a guidewire. No guidewire is shown within guidewire cannula 470. Catheter assembly 400 may be an over-the-wire (OTW) configuration or rapid exchange (RX) type catheter assembly. FIG. 4 illustrates an OTW type catheter assembly.

Catheter assembly 400 also includes delivery cannula 450. In this embodiment, delivery cannula 450 extends from a proximal end of catheter assembly 400 to proximal end or skirt of balloon 430. Balloon 430 is a double layer balloon. Balloon 430 includes inner layer 425 that is a non-porous material, such as Pebax®, Nylon or polyethylene terephthalate (PET). Balloon 430 also includes outer layer 435. Outer layer 435 is a porous material, such as extended polytetrafluoroethylene (ePTFE). In one embodiment, delivery cannula 450 is connected between inner layer 425 and outer layer 435 so that a nitric oxide source can be introduced between the layers and permeate through pores 490 in balloon 430 into a lumen of blood vessel 100.

As illustrated in FIG. 4, in one embodiment, catheter assembly is inserted into blood vessel 100 so that balloon 430 is aligned with treatment site 110. Following alignment of balloon 430 of catheter assembly 400, balloon 430 may be inflated by introducing an inflation medium (e.g., liquid through inflation cannula 460). In one embodiment, balloon 430 is only partially inflated or has an inflated diameter less than an inner diameter of blood vessel 100 at treatment site 110. In this manner, balloon 430 does not contact or only minimally contacts the blood vessel wall. A suitable expanded diameter of balloon 430 is on the order of 2.0 mm to 5.0 mm for coronary vessels. It is appreciated that the expanded diameter may be different for peripheral vasculature. Following the expansion of balloon 430, a substance, such as nitric oxide source, is introduced into delivery cannula 450. The source flows through delivery cannula 450 into a volume between inner layer 425 and outer layer 435 of balloon 430. At a relatively low pressure (e.g., on the order of from about two to about four atmospheres (atm)), the nitric oxide source then permeate through the porous of outer layer 430 into blood vessel 100.

In any of the above-described embodiments, the nitric oxide source may be delivered to a treatment site through a delivery cannula. In some applications, the delivery cannula may be pre-loaded at the proximal end with a nitric oxide source, which may be a nitric oxide gas, a nitric oxide gas solution (aqueous or non-aqueous), an arginase inhibitor, or a carrier loaded with (a) L-arginine and optionally nitric oxide synthase, (b) a nitric oxide donor and suitable reactant or (c) a nitric oxide generator and suitable catalyst.

Figure 5:
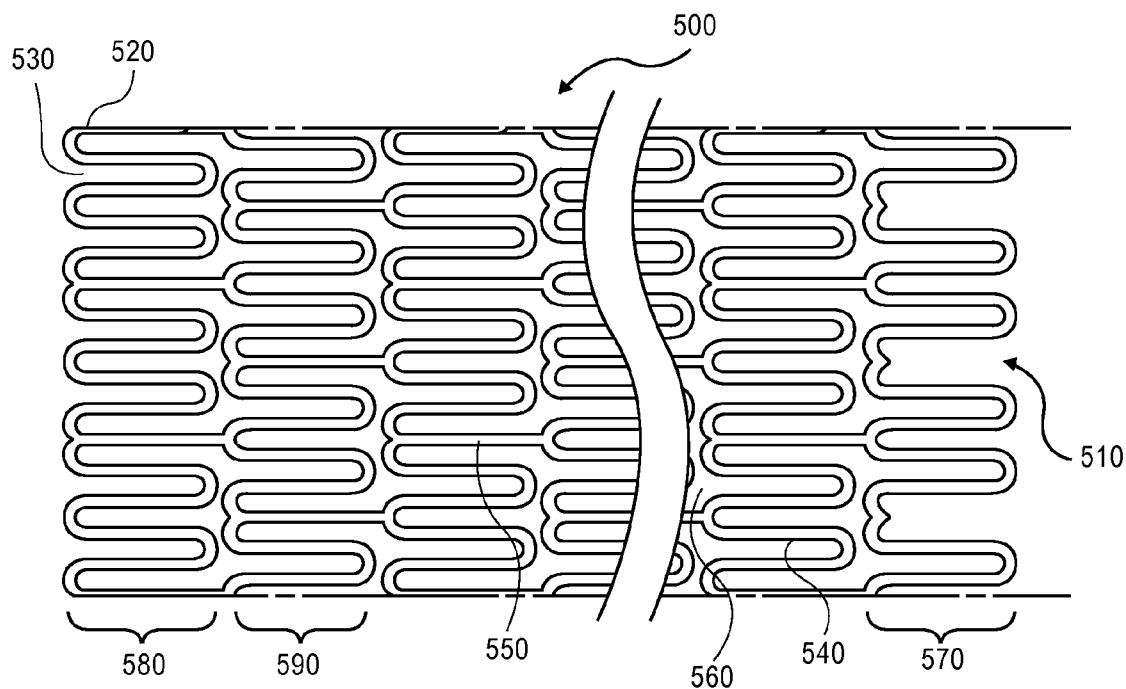
FIG. 5 illustrates an embodiment of a stent which may be used to deliver a nitric oxide source.

In some embodiments, the delivery system can be an implantable medical device deployment system such as a stent deployment system. Representative examples of implantable medical devices include, but are not limited to, self-expandable stents, balloon-expandable stents, micro-depot or micro-channel stents and grafts. FIG. 5 illustrates an embodiment of a stent. Stent 500 is generally tubular and includes a lumen 510 with an abluminal surface 520 and a luminal surface 530. Stent 500 can include a plurality of struts 540 connected by linking struts 550 with interstitial spaces 560 located therebetween. The plurality of struts 540 can be configured in an annular fashion in discrete "rows" such that they form a series of "rings" throughout the body of stent 500. Thus, stent 500 can include proximal ring 570, distal ring 580 and at least one central ring 590. Stent 500 can be metal, polymeric or any other suitable biocompatible material.

In some embodiments, a stent may be fabricated from a biocompatible metal or metal alloy. Representative examples include, but are not limited to, stainless steel (316L or 300), MP35N, MP2ON, Nitinol, Egiloy, tantalum, tantalum alloy, cobalt-chromium alloy, nickel-titanium alloy, platinum, iridium, platinum-iridium alloy, gold, magnesium or combinations thereof. MP35N and MP2ON are trade names for alloys of cobalt, nickel, chromium and molybdenum available from Standard Press Steel Co., Jenkintown, Pa. MP35N consists of 35 percent (%), cobalt, 35% nickel, 20% chromium and 10% molybdenum. MP2ON consists of 50% cobalt, 20% nickel, 20% chromium and 10% molybdenum.

In some embodiments, the stent can be coated with a biocompatible coating which includes a nitric oxide source. The nitric oxide source may or may not be encapsulated in a sustained-release carrier or an activated-release carrier such as those described previously. Representative examples of polymers that may be used to manufacture or coat a stent, include but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile styrene copolymers, ABS resins, polyamides (such as Nylon 66 and polycaprolactam), polycarbonates, polyoxymethylenes, polyimides, polyethers, polyurethanes, rayon, rayon-tracetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in manufacturing or coating stents include ethylene vinyl alcohol copolymer (e.g., EVOH or EVAL), poly(butyl methacrylate), poly(vinylidene fluoride-co-hexfluorapropene (e.g., SOLEF 21708, available from Solvay Solexis PVDF, Thorofare, N.J.), polyvinylidene fluoride (e.g., KYNAR, available from ATOFINA Chemicals, Philadelphia, Pa.), ethylene-vinyl acetate copolymers and polyethylene glycol.

In some applications, a polymer coating comprising at least one layer including a nitric oxide source can be applied to a surface of a stent for controlled release of the nitric oxide source. For example, a coating can include one or a combination of the following types of layers: (a) a treatment agent layer, which may include a polymer and a treatment agent, or alternatively, a polymer-free treatment agent; (b) an optional primer layer, which may improve adhesion of subsequent layers on the stent or on a previously formed layer; (c) an optional topcoat layer, which may serve to control the rate of release of the treatment agent; and (d) an optional biocompatible finishing layer, which may improve the biocompatibility of the coating. The treatment agent can be a nitric oxide source.

In some embodiments, the coating can be partially or completely applied to an abluminal surface or a luminal surface of the stent. The coating can be applied by methods known by those skilled in the art, including, but not limited to, dipping, spraying, pouring, brushing, spin-coating, roller coating, meniscus coating, powder coating, drop-on-demand coating, sputtering, gas-phase polymerization, solvent inversion or any combination thereof. Coating techniques are known by those skilled in the art.

In some embodiments, a stent may be fabricated from a bioerodable or biodegradable polymer to form a polymeric stent. Manufacturing processes for forming a polymeric stent include, but are not limited to, casting, molding or combinations thereof. Casting involves pouring a liquid polymeric composition into a mold. Molding processes include, but are not limited to, compression molding, extrusion molding, injection molding and foam molding. In compressing molding, solid polymeric materials are added to a mold and pressure and heat are applied until the polymeric material conforms to the mold. In extrusion molding, solid polymeric materials are added to a continuous melt that is forced through a die and cooled to a solid form. In injection molding, solid polymeric materials are added to a heated cylinder, softened and forced into a mold under pressure to create a solid form. In foam molding, blowing agents are used to expand and mold solid polymeric materials into a desired form, and the solid polymeric materials can be expanded to a volume in a range from about 2 to 50 times their original volume. In the above-described molding embodiments, the solid form may require additional processing to obtain the final product in a desired form.

In some embodiments, a nitric oxide source may be directly incorporated into the body of a polymeric stent during the manufacturing process. For example, a nitric oxide source may be combined with a polymer matrix and subsequently subjected to any of the above-described manufacturing process for formation thereof. In this aspect, the nitric oxide source may be released in a controlled manner as the polymeric stent naturally degrades over time.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

What is claimed is:

1. A composition for inducing cell apoptosis at an atherosclerotic lesion in a blood vessel, comprising:
    a mixture having a solvent and an amount of nitric oxide dissolved in the solvent, wherein the solvent is an aqueous solution selected from the group consisting of saline and physiological buffer, and wherein the aqueous solution is saturated with the amount of nitric oxide; and
    a microsphere dispersed in the mixture, the microsphere having a polymer encapsulant encapsulating an unbound nitric oxide gas prior to being dispersed in the mixture; and
    wherein the mixture is suitable for delivery into a blood vessel to deliver the microsphere to a cell in an atherosclerotic lesion in the blood vessel.

2. The composition of claim 1, wherein the polymer encapsulant comprises poly(caprolactone).

3. The composition of claim 1, wherein the amount of nitric oxide is less than about three thousandths of a mole per liter of the mixture.

4. The composition of claim 1, wherein the mixture further comprises a surfactant selected from the group consisting of poly vinyl alcohol, poly vinyl pyrrolidone, lipids, amphiphilic polymers, and ionic surfactants.

5. A treatment kit comprising:
    a delivery device comprising a catheter assembly having a delivery cannula, wherein the catheter assembly is sized and configured for insertion into a blood vessel; and
    a nitric oxide source comprising a mixture having a solvent and an amount of nitric oxide dissolved in the solvent, and a microsphere dispersed in the mixture, the microsphere having a polymer encapsulant encapsulating an unbound nitric oxide gas prior to being dispersed in the mixture, wherein the solvent is an aqueous solution selected from the group consisting of saline and physiological buffer, wherein the aqueous solution is saturated with the amount of nitric oxide, and wherein the nitric oxide source is suitable for delivery through the delivery cannula into the blood vessel.

6. The treatment kit of claim 5, wherein the polymer encapsulant comprises poly(caprolactone).

7. The treatment kit of claim 5, wherein the amount of nitric oxide is less than about three thousandths of a mole per liter of the mixture.

8. The treatment kit of claim 5, wherein the mixture further comprises a surfactant selected from the group consisting of poly vinyl alcohol, poly vinyl pyrrolidone, lipids, amphiphilic polymers, and ionic surfactants.

* * * * *